US012002462B2

(12) United States Patent
Chao et al.

(10) Patent No.: US 12,002,462 B2
(45) Date of Patent: Jun. 4, 2024

(54) VOICE COMMAND HANDLER FOR PROGRAMMING STIMULATION SYSTEMS AND METHODS OF USING

(71) Applicant: Boston Scientific Neuromodulation Corporation, Valencia, CA (US)

(72) Inventors: Jimmy Lee Chao, Long Beach, CA (US); Vishal Jagannathan, Santa Clarita, CA (US); Eugene Mesina, Canyon Country, CA (US); Travis McCoy, Slidell, LA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 217 days.

(21) Appl. No.: 17/513,382

(22) Filed: Oct. 28, 2021

(65) Prior Publication Data
US 2022/0148591 A1     May 12, 2022

Related U.S. Application Data

(60) Provisional application No. 63/112,537, filed on Nov. 11, 2020.

(51) Int. Cl.
*G10L 15/26*     (2006.01)
*G10L 15/22*     (2006.01)

(52) U.S. Cl.
CPC .............. *G10L 15/22* (2013.01); *G10L 15/26* (2013.01); *G10L 2015/223* (2013.01)

(58) Field of Classification Search
CPC ............ A61N 1/37211; A61N 1/37247; A61N 1/37282; A61N 1/36135; A61N 1/36139;
(Continued)

(56) References Cited

U.S. PATENT DOCUMENTS 5,792,204 A    8/1998 Snell
6,181,969 B1   1/2001 Gord
(Continued)

OTHER PUBLICATIONS

International Search Report and Written Opinion for PCT Application No. PCT/US2021/057059 dated Mar. 3, 2022.
U.S. Appl. No. 63/109,749, filed Nov. 4, 2020.

*Primary Examiner* — Md S Elahee
(74) *Attorney, Agent, or Firm* — Branch Partners PLLC; Bruce E. Black

(57) ABSTRACT

A method for programming a stimulation device of a stimulation system using a programming device includes providing a set of programming commands for the programming device that include a first programming command increasing a stimulation amplitude and a second programming command includes decreasing the stimulation amplitude; receiving a verbal communication by a voice command handler of the programming device or in communication with the programming device; determining whether the verbal communication is a trigger word and, when the verbal communication is the trigger word, entering a triggered state, wherein, after entering the triggered state, the programming device remains in the triggered state until a one of at least one stop condition is met; and, when in the triggered state, determining whether the verbal communication is one of the programming commands and, when the verbal communication is one of the programming commands, executing the one of the programming commands.

17 Claims, 7 Drawing Sheets

(58) Field of Classification Search
CPC ... G10L 15/22; G10L 15/26; G10L 2015/223; E03C 1/052; G01B 3/205
USPC ........................................................ 704/235
See application file for complete search history.

(56) References Cited

U.S. PATENT DOCUMENTS

| | | |
|---|---|---|
| 6,295,944 B1 | 10/2001 | Lovett |
| 6,391,985 B1 | 5/2002 | Goode et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,895,280 B2 | 5/2005 | Meadows et al. |
| 7,244,150 B1 | 7/2007 | Brase et al. |
| 7,319,962 B2 | 1/2008 | Goedeke et al. |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,483,237 B2 | 7/2013 | Zimmermann et al. |
| 8,688,235 B1 | 4/2014 | Pianca et al. |
| 8,706,251 B2 | 4/2014 | Von Arx et al. |
| 8,831,742 B2 | 9/2014 | Pianca et al. |
| 9,275,637 B1 | 3/2016 | Salvador et al. |
| 9,474,903 B2 | 10/2016 | Chen et al. |
| 9,561,380 B2 | 2/2017 | Carcieri et al. |
| 9,592,389 B2 | 3/2017 | Moffitt |
| 9,643,014 B2 | 5/2017 | Zhang et al. |
| 9,643,017 B2 | 5/2017 | Carcieri et al. |
| 9,781,086 B2 | 10/2017 | Jelatis et al. |
| 9,959,388 B2 | 5/2018 | Grandhe et al. |
| 10,071,249 B2 | 9/2018 | Zottola |
| 10,350,404 B2 | 7/2019 | Zhang et al. |
| 10,441,800 B2 | 10/2019 | Steinke |
| 10,603,498 B2 | 3/2020 | Blum et al. |
| 10,625,082 B2 | 4/2020 | Laghi |
| 10,716,505 B2 | 7/2020 | Blum et al. |
| 10,716,942 B2 | 7/2020 | Zhang |
| 10,744,330 B2 | 8/2020 | Moffitt et al. |
| 10,780,282 B2 | 9/2020 | Mustakos et al. |
| 2007/0043401 A1 | 2/2007 | John |
| 2007/0067004 A1 | 3/2007 | Boveja et al. |
| 2007/0150036 A1 | 6/2007 | Anderson |
| 2009/0105785 A1 | 4/2009 | Wei et al. |
| 2009/0187222 A1 | 7/2009 | Barker |
| 2009/0276021 A1 | 11/2009 | Meadows et al. |
| 2010/0023090 A1 | 1/2010 | Jaax et al. |
| 2010/0076535 A1 | 3/2010 | Pianca et al. |
| 2010/0268298 A1 | 10/2010 | Moffitt et al. |
| 2011/0004267 A1 | 1/2011 | Meadows |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0188096 A1 | 7/2012 | Corndorf et al. |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0203366 A1 | 8/2012 | Saliger et al. |
| 2012/0316615 A1 | 12/2012 | DiGiore et al. |
| 2013/0054246 A1* | 2/2013 | Newman ............... G01B 3/205 704/E11.001 |
| 2013/0105071 A1 | 5/2013 | DiGiore et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317572 A1 | 11/2013 | Zhu et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0012341 A1 | 1/2014 | Von Arx et al. |
| 2014/0039587 A1 | 2/2014 | Romero |
| 2014/0353001 A1 | 12/2014 | Romero et al. |
| 2014/0353501 A1 | 12/2014 | Fantone et al. |
| 2014/0358024 A1 | 12/2014 | Nelson et al. |
| 2014/0358207 A1 | 12/2014 | Romero |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0151113 A1 | 6/2015 | Govea et al. |
| 2015/0306391 A1 | 10/2015 | Wu et al. |
| 2015/0348554 A1 | 12/2015 | Orr et al. |
| 2017/0225007 A1 | 8/2017 | Orinski |
| 2017/0259078 A1 | 9/2017 | Howard |
| 2018/0110971 A1 | 4/2018 | Serrano Carmona |
| 2018/0369606 A1 | 12/2018 | Zhang et al. |
| 2018/0369607 A1 | 12/2018 | Zhang et al. |
| 2019/0036886 A1 | 1/2019 | Wu et al. |
| 2019/0156818 A1 | 5/2019 | Piersol et al. |
| 2019/0209834 A1 | 7/2019 | Zhang et al. |
| 2019/0209849 A1 | 7/2019 | Hershey et al. |
| 2019/0292758 A1* | 9/2019 | Warsowe ............... E03C 1/052 |
| 2020/0094047 A1 | 3/2020 | Govea et al. |
| 2020/0139140 A1 | 5/2020 | Crawford |
| 2020/0155854 A1 | 5/2020 | Leven et al. |
| 2020/0305716 A1 | 10/2020 | Mondello et al. |
| 2020/0376262 A1 | 12/2020 | Clark et al. |
| 2021/0023374 A1 | 1/2021 | Block et al. |
| 2021/0316139 A1 | 10/2021 | Shelton et al. |
| 2022/0096848 A1* | 3/2022 | Hareland ............ A61N 1/36135 |
| 2023/0181906 A1 | 6/2023 | Moore et al. |

* cited by examiner

VOICE COMMAND HANDLER FOR PROGRAMMING STIMULATION SYSTEMS AND METHODS OF USING

CROSS-REFERENCE TO RELATED APPLICATIONS

This application claims the benefit under 35 U.S.C. § 119(e) of U.S. Provisional Patent Application Ser. No. 63/112,537, filed Nov. 11, 2020, which is incorporated herein by reference.

FIELD

The present disclosure is directed to the area of methods and systems including a voice command handler for stimulation systems. The present disclosure is also directed to methods and systems including a voice command handler for programming stimulation systems.

BACKGROUND

Implantable electrical stimulation systems have proven therapeutic in a variety of diseases and disorders. For example, deep brain stimulation systems have been used as a therapeutic modality for the treatment of Parkinson's disease, essential tremor, and the like.

Stimulators have been developed to provide therapy for a variety of treatments. A stimulator can include an implantable pulse generator (IPG), one or more leads, and an array of stimulator electrodes on each lead. The stimulator electrodes are in contact with or near the nerves, muscles, or other tissue to be stimulated. The pulse generator in the IPG generates electrical pulses that are delivered by the electrodes to body tissue.

Implantable medical devices (IMDs), including IPGs, typically have the capability to communicate data with an external device, such as a clinician programmer or a remote control, via a radio-frequency telemetry link or other wireless communication method. The clinician programmer can program the operating parameters of the implanted medical device. The remote control can switch programs. Modern implantable devices also include the capability for bidirectional communication so that information can be transmitted to the clinician programmer or remote control from the implanted device.

BRIEF SUMMARY

One aspect is a method for programming a stimulation device of a stimulation system using a programming device. The method includes providing a set of programming commands for the programming device, wherein the programming commands include a first programming command increasing a stimulation amplitude and a second programming command includes decreasing the stimulation amplitude; receiving a verbal communication by a voice command handler of the programming device or in communication with the programming device; determining whether the verbal communication is a trigger word and, when the verbal communication is the trigger word, entering a triggered state, wherein, after entering the triggered state, the programming device remains in the triggered state until a one of at least one stop condition is met; and, when in the triggered state, determining whether the verbal communication is one of the programming commands and, when the verbal communication is one of the programming commands, executing the one of the programming commands, wherein the at least one stop condition includes at least one of: (1) not receiving verbal communication for a predefined time period of at least 10 seconds, or (2) receiving a predefined number of consecutive verbal communications that are not any of the programming commands.

In at least some aspects, the predefined time period is at least 15 seconds. In at least some aspects, the predefined number is at least three.

In at least some aspects, determining whether the verbal communication is one of the programming commands includes comparing the verbal communication to the predefined set of programming commands. In at least some aspects, the set of programming commands includes a plurality of single word commands. In at least some aspects, the set of programming commands includes a plurality of multi-word commands. In at least some aspects, at least one of the multi-word commands has a form of a command phrase and a user-selected number.

In at least some aspects, the method further includes converting the verbal communication to a machine-readable text. In at least some aspects, the method further includes delivering the verbal communication to a service provider for the purpose of converting the verbal communication to a machine-readable test and receiving, from the service provider, the machine-readable text. In at least some aspects, the method further includes providing an audible or visual indication after executing the one of the programming commands.

Another aspect is a method for programming a stimulation device of a stimulation system using a programming device. The method includes providing a predefined set of programming commands for the programming device, wherein the predefined set of programming commands include a plurality of single word commands and a plurality of multi-word commands, wherein the single word commands include a first programming command increasing a stimulation amplitude and a second programming command includes decreasing the stimulation amplitude; receiving a verbal communication by a voice command handler of the programming device or in communication with the programming device; determining whether the verbal communication is a trigger word and, when the verbal communication is the trigger word, entering a triggered state, wherein, after entering the triggered state, the programming device remains in the triggered state until a one of at least one stop condition is met; when in the triggered state, determining whether the verbal communication is one of the single word commands and, when the verbal communication is one of the single word commands, executing the one of the single word commands and remaining in the triggered state; and, when in the triggered state, determining whether the verbal communication is one of the multi-word commands and, when the verbal communication is one of the multi-word commands, executing the one of the multi-word commands and entering a non-triggered state.

In at least some aspects, the at least one stop condition includes not receiving verbal communication for a predefined time period of at least 15 seconds. In at least some aspects, the at least one stop condition includes receiving a predefined number of consecutive verbal communications that are not the trigger word, any of the single word commands, or any of the multi-word commands, wherein the predefined number is at least three. In at least some aspects, at least one of the multi-word commands has a form of a command phrase and a user-selected number.

In at least some aspects, the method further includes converting the verbal communication to a machine-readable text. In at least some aspects, the method further includes delivering the verbal communication to a service provider for the purpose of converting the verbal communication to a machine-readable test and receiving, from the service provider, the machine-readable text. In at least some aspects, the method further includes providing an audible or visual indication after executing the one of the single word commands or the one of the multi-word commands.

Yet another aspect is a method for programming a stimulation device of a stimulation system using a programming device. The method includes providing a set of programming commands for the programming device, wherein the programming commands include a first programming command increasing a stimulation amplitude and a second programming command includes decreasing the stimulation amplitude; receiving a verbal communication by a voice command handler of the programming device or in communication with the programming device; determining whether a voice command handler actuator has been actuated prior to the verbal communication; and, when the voice command handler actuator has been actuated prior to the verbal communication by no more than a predetermined time period, determining whether the verbal communication is one of the programming commands and, when the verbal communication is one of the programming commands, executing the one of the programming commands.

In at least some aspects, the predefined time period is at least 5 seconds. In at least some aspects, the voice command handler actuator is a foot pedal.

A further aspect is a programming device configured for programming a stimulation device of a stimulation system. The programming device includes a memory having stored thereon instructions and a processor coupled to the memory and configured to execute the instructions to perform actions. The actions include providing a set of programming commands, wherein the programming commands include a first programming command increasing a stimulation amplitude and a second programming command includes decreasing the stimulation amplitude; receiving a verbal communication; determining whether the verbal communication is a trigger word and, when the verbal communication is the trigger word, entering a triggered state, wherein, after entering the triggered state, the programming device remains in the triggered state until a one of at least one stop condition is met; and, when in the triggered state, determining whether the verbal communication is one of the programming commands and, when the verbal communication is one of the programming commands, executing the one of the programming commands.

In at least some aspects, the at least one stop condition includes not receiving verbal communication for a predefined time period of at least 10, 15, 30, or 60 seconds. In at least some aspects, the at least one stop condition includes receiving a predefined number of consecutive verbal communications that are not the trigger word or any of the programming commands, wherein the predefined number is at least three.

In at least some aspects, determining whether the verbal communication is one of the programming commands includes comparing the verbal communication to the predefined set of programming commands. In at least some aspects, the set of programming commands includes a plurality of single word commands. In at least some aspects, the set of programming commands includes a plurality of multi-word commands. In at least some aspects, at least one of the multi-word commands has a form of a command phrase and a user-selected number.

In at least some aspects, the instructions further include converting the verbal communication to a machine-readable text. In at least some aspects, the instructions further include delivering the verbal communication to a service provider for the purpose of converting the verbal communication to a machine-readable test and receiving, from the service provider, the machine-readable text. In at least some aspects, the instructions further include providing an audible or visual indication after executing the one of the programming commands.

Another aspect is a programming device configured for programming a stimulation device of a stimulation system. The programming device includes a memory having stored thereon instructions and a processor coupled to the memory and configured to execute the instructions to perform actions. The actions include providing a predefined set of programming commands, wherein the predefined set of programming commands include a plurality of single word commands and a plurality of multi-word commands, wherein the single word commands include a first programming command increasing a stimulation amplitude and a second programming command includes decreasing the stimulation amplitude; receiving a verbal communication; determining whether the verbal communication is a trigger word and, when the verbal communication is the trigger word, entering a triggered state, wherein, after entering the triggered state, the programming device remains in the triggered state until a one of at least one stop condition is met; when in the triggered state, determining whether the verbal communication is one of the single word commands and, when the verbal communication is one of the single word commands, executing the one of the single word commands and remaining in the triggered state; and, when in the triggered state, determining whether the verbal communication is one of the multi-word commands and, when the verbal communication is one of the multi-word commands, executing the one of the multi-word commands and entering a non-triggered state. In at least some aspects, a user can add a programming command to the predefined set of programming commands or modify a programming command in the predefined set of programming commands.

In at least some aspects, the at least one stop condition includes not receiving verbal communication for a predefined time period of at least 15 seconds. In at least some aspects, the at least one stop condition includes receiving a predefined number of consecutive verbal communications that are not the trigger word, any of the single word commands, or any of the multi-word commands, wherein the predefined number is at least three.

In at least some aspects, at least one of the multi-word commands has a form of a command phrase and a user-selected number. In at least some aspects, the instructions further include converting the verbal communication to a machine-readable text. In at least some aspects, the instructions further include delivering the verbal communication to a service provider for the purpose of converting the verbal communication to a machine-readable test and receiving, from the service provider, the machine-readable text. In at least some aspects, the instructions further include providing an audible or visual indication after executing the one of the single word commands or the one of the multi-word commands.

Yet another aspect is a programming arrangement for a stimulation system. The programming arrangement includes a voice command handler actuator configured for user actuation; and a programming device coupled, or coupleable to, the voice command handler actuator and configured for programming a stimulation device of the stimulation system. The programing device includes a memory having stored thereon instructions and a processor coupled to the memory and configured to execute the instructions to perform actions. The actions include providing a set of programming commands, wherein the programming commands include a first programming command increasing a stimulation amplitude and a second programming command includes decreasing the stimulation amplitude; receiving a verbal communication; determining whether the voice command handler actuator has been actuated prior to the verbal communication; and, when the voice command handler actuator has been actuated prior to the verbal communication, determining whether the verbal communication is one of the programming commands and, when the verbal communication is one of the programming commands, executing the one of the programming commands.

In at least some aspects, determining whether the voice command handler actuator has been actuated includes determining whether the voice command handler actuator has been actuated prior to the verbal communication by no more than a predefined time period. In at least some aspects, the voice command handler actuator is a foot pedal.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of methods and systems including a voice command handler for stimulation systems. The present disclosure is also directed to methods and systems including a voice command handler for programming stimulation systems.

Implantable electrical stimulation systems and devices are used herein to exemplify the inventions, but it will be understood that these inventions can be utilized with other stimulation systems and devices. Examples of implantable electrical stimulation systems include, but are not limited to, a least one lead with one or more electrodes disposed along a distal end of the lead and one or more terminals disposed along the one or more proximal ends of the lead. Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 8,175,710; 8,224,450; 8,271,094; 8,295,944; 8,364,278; and 8,391,985; U.S. Patent Application Publications Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties.

Figure 1:
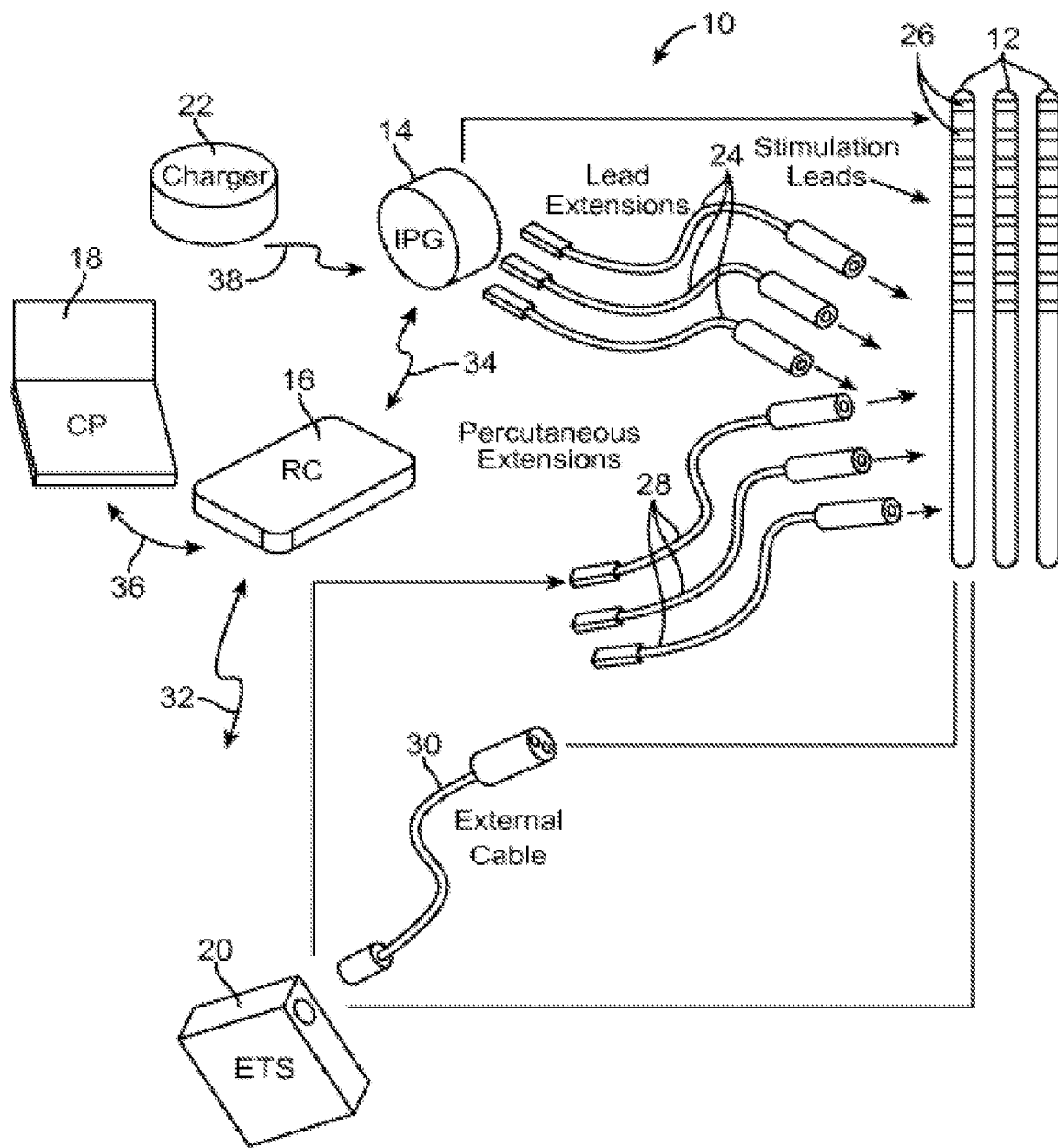
FIG. 1 is a schematic view of one embodiment of an electrical stimulation system that includes one or more leads that can be coupled to an IPG.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22. The IPG and ETS are examples of control modules for the electrical stimulation system.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's abdominal cavity or at any other suitable site. The implantable pulse generator 14 can have multiple stimulation channels which may be independently programmable to control the magnitude of the current stimulus from each channel. In some embodiments, the implantable pulse generator 14 can have any suitable number of stimulation channels including, but not limited to, 4, 6, 8, 12, 16, 32, or more stimulation channels. The implantable pulse generator 14 can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14, for example, to be turned on or off and to be programmed with different stimulation parameter sets. The IPG 14 may also be operated to modify the programmed stimulation parameters to actively control the characteristics of the electrical stimulation energy output by the IPG 14. In at least some embodiments, the CP 18 (or ETS 20 or RC 16 or other programming device) allows a user, such as a clinician, the ability to program stimulation parameters for the IPG 14 and ETS 20 in the operating room and in follow-up sessions. Alternately, or additionally, in at least some embodiments, stimulation parameters can be programed via wireless communications (e.g., Bluetooth) between the RC 16 (or other external device such as a hand-held electronic device like a mobile phone, tablet, or the like) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). In at least some embodiments, the stimulation parameters provided by the CP 18 are also used to program the RC 16, so that the stimulation parameters can be subsequently modified by operation of the RC 16 in a stand-alone mode (i.e., without the assistance of the CP 18). The CP 18, RC 16, or ETS 20 can be any suitable device including, but not limited to, a computer or other computing device, laptop, mobile device (for example, a mobile phone or tablet), or the like or any combination thereof. The CP 18, RC 16, or ETS 20 can include software applications for interacting with the IPG 14 and for programming the IPG 14.

Additional examples of the RC 16, CP 18, ETS 20, and external charger 22 can be found in the references cited herein as well as U.S. Pat. Nos. 6,895,280; 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, all of which are incorporated herein by reference in their entireties.

Figure 2:
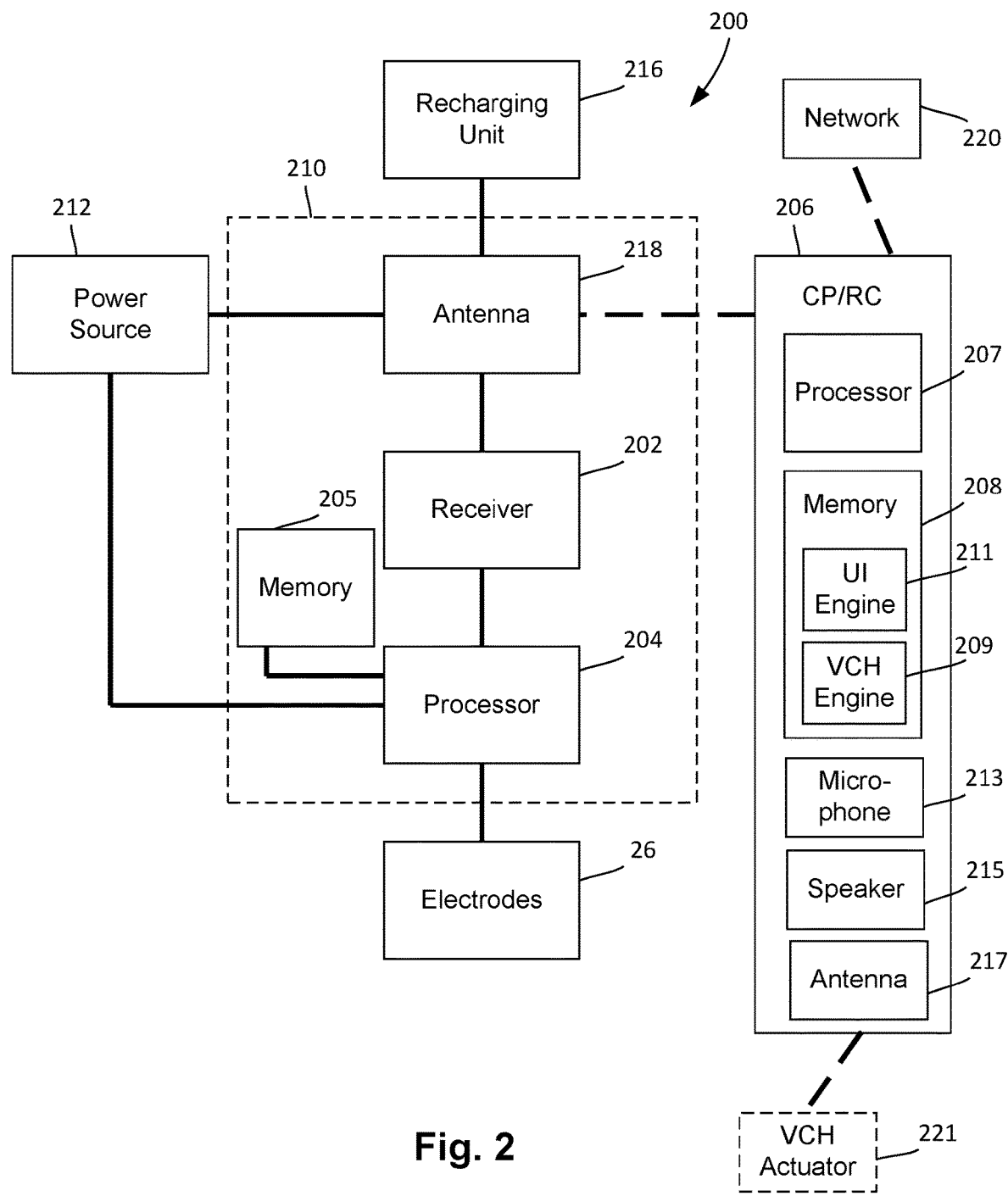
FIG. 2 is a block diagram of element of an electrical stimulation system.

FIG. 2 is a schematic overview of one embodiment of components of an electrical stimulation system 200 including an electronic subassembly 210 disposed within an IPG 14 (FIG. 1). It will be understood that the electrical stimulation system can include more, fewer, or different components and can have a variety of different configurations including those configurations disclosed in the stimulator references cited herein.

The IPG 14 (FIG. 1) can include, for example, a power source 212, antenna 218, receiver 202, processor 204, and memory 205. An external device, such as a CP or RC 206, can include a processor 207 and memory 208. Some of the components (for example, power source 212, antenna 218, receiver 202, processor 204, and memory 205) of the electrical stimulation system can be positioned on one or more circuit boards or similar carriers within a sealed housing of the IPG 14 (FIG. 1), if desired. Any power source 212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference in its entirety.

As another alternative, power can be supplied by an external power source through inductive coupling via the optional antenna 218 or a secondary antenna. The external power source can be in a device that is mounted on the skin of the user or in a unit that is provided near the user on a permanent or periodic basis.

If the power source 212 is a rechargeable battery, the battery may be recharged using the optional antenna 218, if desired. Power can be provided to the battery for recharging by inductively coupling the battery through the antenna to a recharging unit 216 external to the user. Examples of such arrangements can be found in the references identified above.

In one embodiment, electrical current is emitted by the electrodes 26 on the lead body to stimulate nerve fibers, muscle fibers, or other body tissues near the electrical stimulation system. A processor 204 is generally included to control the timing and electrical characteristics of the electrical stimulation system. For example, the processor 204 can, if desired, control one or more of the timing, frequency, amplitude, width, and waveform of the pulses. In addition, the processor 204 can select which electrodes can be used to provide stimulation, if desired. In some embodiments, the processor 204 may select which electrode(s) are cathodes and which electrode(s) are anodes. In some embodiments, the processor 204 may be used to identify which electrodes provide the most useful stimulation of the desired tissue. Instructions for the processor 204 can be stored on the memory 205. Instructions for the processor 207 can be stored on the memory 208.

Any processor 204 can be used for the IPG and can be as simple as an electronic device that, for example, produces pulses at a regular interval or the processor can be capable of receiving and interpreting instructions from the CP/RC 206 (such as CP 18 or RC 16 of FIG. 1) that, for example, allows modification of pulse characteristics. In the illustrated embodiment, the processor 204 is coupled to a receiver 202 which, in turn, is coupled to the optional antenna 218. This allows the processor 204 to receive instructions from an external source to, for example, direct the pulse characteristics and the selection of electrodes, if desired. Any suitable processor 207 can be used for the CP/RC 206.

Any suitable memory 205, 208 can be used including computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include, but are not limited to, RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a processor.

In one embodiment, the antenna 218 is capable of receiving signals (e.g., RF signals) from an antenna 217 of a CP/RC 206 (see, CP 18 or RC 16 of FIG. 1) which is programmed or otherwise operated by a user. The signals sent to the processor 204 via the antenna 218 and receiver 202 can be used to modify or otherwise direct the operation of the electrical stimulation system. For example, the signals may be used to modify the pulses of the electrical stimulation system such as modifying one or more of pulse width, pulse frequency, pulse waveform, and pulse amplitude. The signals may also direct the electrical stimulation system 200 to cease operation, to start operation, to start charging the battery, or to stop charging the battery. In other embodiments, the stimulation system does not include an antenna 218 or receiver 202 and the processor 204 operates as programmed.

Optionally, the electrical stimulation system 200 may include a transmitter (not shown) coupled to the processor 204 and the antenna 218 for transmitting signals back to the CP/RC 206 or another unit capable of receiving the signals. For example, the electrical stimulation system 200 may transmit signals indicating whether the electrical stimulation system 200 is operating properly or not or indicating when the battery needs to be charged or the level of charge remaining in the battery. The processor 204 may also be capable of transmitting information about the pulse characteristics so that a user or clinician can determine or verify the characteristics.

Transmission of signals can occur using any suitable method, technique, or platform including, but not limited to, inductive transmission, radiofrequency transmission, Bluetooth™, Wi-Fi, cellular transmission, near field transmission, infrared transmission, or the like or any combination thereof. In addition, the IPG 14 can be wirelessly coupled to the RC 16 or CP 18 using any suitable arrangement include direct transmission or transmission through a network, such as a local area network, wide area network, the Internet, or the like or any combination thereof. The CP 18 or RC 16 may also be capable of coupling to, and sending data or other information to, a network 220, such as a local area network, wide area network, the Internet, or the like or any combination thereof.

Returning to FIG. 1, the CP 18 or RC 16 (or other external device) utilizes software applications to communicate with the IPG 14. These software applications are often custom-made and instructions for the software applications can be stored in the memory of the CP, RC, or other external device. In at least some embodiments, depending on its purpose, each software application may have a capability (or permission) to perform one or more of the following: read data, write data, select from existing programs, modify programming settings of existing programs, create programs, modify or update software/firmware, full control (which could include all of the previously listed capabilities), or otherwise interact with the IPG or any combination of these capabilities (or permissions).

In addition, the methods, techniques, and systems described herein are presented in the context of an electrical stimulation system, but it will be recognized that these methods, techniques, and systems can be used with an optical stimulation system or an electrical/optical stimulation system. Examples of optical stimulation systems or electrical/optical stimulation systems are found in U.S. Patent Application Publications Nos. 2013/0317572; 2013/0317573; 2017/0259078; 2017/0225007; 2018/0110971; 2018/0369606; 2018/0369607; 2019/0209849; 2019/0209834; 2020/0094047; and 2020/0155854 and U.S. patent application Ser. No. 16/883,404, all of which are incorporated herein by reference in their entireties.

Programming an IPG to provide patient therapy can be a time-consuming process as the clinician tests different electrodes or electrode combinations and different stimulation settings (for example, amplitude, pulse width, pulse frequency, or the like or any combination thereof). Often, after each selection of electrode(s) and stimulation settings, the clinician determines the effect of the stimulation by observation, patient feedback, sensor feedback, or the like or any combination thereof. In some cases, a clinician has an assistant make programming changes as the clinician determines the effect of the stimulation. In other cases, the clinician may go back and forth from the programming device (such as a CP or RC) to change stimulation settings/electrode selection and the patient to determine the effect of the stimulation.

A programming session can take longer due to the amount of time the clinician takes to locate and find the correct programming parameters or due to miscommunication between the assistant and clinician when changing programming parameters. Longer programming sessions may lead to prolonged pain, a less than satisfactory programming session, or agitation or frustration from the patient or, in some instances, the clinician. A patient may feel frustration due to the length of the programming session or because it appears that the clinician is paying more attention to the programming device than the patient. A clinician may feel frustration as the clinician searches through the user interface to find the right stimulation settings before checking with the patient. A clinician may also forget or not have time to use tools, such as a clinical effects map or recording mechanism, that could improve programming results. In addition, a clinician may want to have real-time programming session in which the clinician is able to quickly change a stimulation parameter, preferably without turning off the stimulation first.

In contrast to conventional electrical stimulation systems, the methods and stimulation systems described herein can include an automated voice command handler to facilitate programming of the system. In at least some embodiments, as illustrated in FIG. 2, the instructions for a voice command handler (VCH) engine 209 and a user interface (UI) engine 211 are stored in the memory 208 of the CP/RC 206 and executed by the processor 207 to provide a voice command handler and user interface for the CP or RC. Non-limiting examples of user interfaces can be found at, for example, U.S. Pat. Nos. 9,474,903; 9,592,389; 9,561,380; 10,350,404; 10,625,082; 10,744,330; and 10,780,282, all of which are incorporated herein by reference in their entireties.

As described herein, the stimulation system can include a voice command handler (which may also be referred to as a voice command assistant) that allows clinicians to program stimulation or modify programming of stimulation by voice command in real time. The voice command handler can substitute for programming, modifying stimulation parameters or settings or executing other commands by hand (either the clinician's or assistant's hand) using the programming device (such as a CP or RC). The voice command handler responds to keywords spoken by the clinician (or other programmer) and directs the programming device (such as a CP or RC) to enact the programming command associated with the keyword. Unless otherwise indicated a "programming command" is any command of the programming device including, but not limited to, the selection or modification of stimulation parameters, electrode selection, or other settings (for example, the recording or modification of therapeutic or side effects, changes to visual or other aspects of the user interface of the programming device, changes to the operation or mode of the programming device or the like.)

In at least some embodiments, the voice command handler provides for hands-free interactive programming which may allow the clinician to focus more on the patient and less on the screen of the programming device. The voice command handler may allow for more patient interaction reducing the amount of interaction with the screen and controls of the programming device and increasing the amount of time spent understanding the results of the current stimulation with the patient. In at least some embodiments, the voice command handler may allow the clinician to be able to program stimulation in real time efficiently. In at least some embodiments, to program in real-time is to change a stimulation setting or steer the stimulation without turning off the stimulation prior to the change. To program efficiently can address the tedious nature of the stimulation programming session where there may be a multitude of button clicks needed for some commands.

A CP will be utilized in the description as the programming device that includes a voice command handler, but it will be understood that the CP could be replaced by any other suitable programming device, such as a computer, laptop, RC, ETS, or the like. In addition, in the description a clinician provides the verbal communication, but it will be understood that the clinician can be replaced by any other user, such as, but not limited to, a programmer, clinician assistant, or the like.

In at least some embodiments, the voice command handler is always active when the CP is on. In other embodiments, the voice command handler must be manually activated on the CP. In at least some embodiments, a user can deactivate the voice command handler. In at least some embodiments, when the voice command handler is active, the voice command handler is by default in an always-listening state where it will record and listen to all spoken language caught by a microphone 213 (FIG. 2) of the CP. In other embodiments, the listening mode must be manually activated. To activate a command, a trigger word is said prior to issuing one or more commands. In at least some embodiments, when the trigger word is received and recognized, the CP enters a triggered state for receiving and executing programming commands. When a stop condition is met, the CP enters a non-triggered state and stops receiving and executing programming commands until the trigger word is used again.

Many voice command arrangements require a trigger word prior to each individual command or query to activate the voice command arrangement and indicate that the command or query should be acted upon. In contrast, in at least some embodiments of the methods and systems described herein, the voice command handler of the stimulation system does not require using a trigger word to activate the voice command handler with each programming command, but rather, after initial activation with a trigger word, the voice command handler continues to act on multiple sequential programming commands until a stop condition is achieved. For example, after using the trigger word, the clinician could speak the programming commands "Increase, Increase, Increase" causing the CP to increase the amplitude of the stimulation by three default amounts. In at least some embodiments, the stop condition is a determination that natural language is taking place rather than programming commands being issued. In at least some embodiments, the stop condition is a determination that a predetermined period of silence (for example, 10, 15, 30, or 45 seconds or 1, 2, 5, 10, or 15 minutes) has occurred.

In at least some embodiments, the voice command handler does not require the trigger word before each sequential single word command after the initial activation with a trigger word, but the voice command handler may require the trigger word before each multi-word command.

In at least some embodiments, the voice command handler after receiving the trigger word is prepared to receive either a single word command or a multi-word command. If a single word command is received the voice command handler is prepared to receive sequential single word commands until a stop condition is reached. If a multi-word command is received the voice command handler must receive the trigger word again for the next command.

Many voice command arrangements wait for a quiescent period (e.g., a period of silence) before beginning the parsing of the voice command. In contrast, in at least some embodiments of the methods and systems described herein, the voice command handler of the stimulation system begins parsing the voice command without waiting for a quiescent period (for example, a period of time of at least 1, 2, or 5 seconds.) In at least some embodiments, the voice command handler of the stimulation system uses real-time streaming of verbal utterance to enact the voice commands instead of waiting for a quiescent period or period of silence (for example, a period of time of at least 1, 2, or 5 seconds.)

Figure 3:
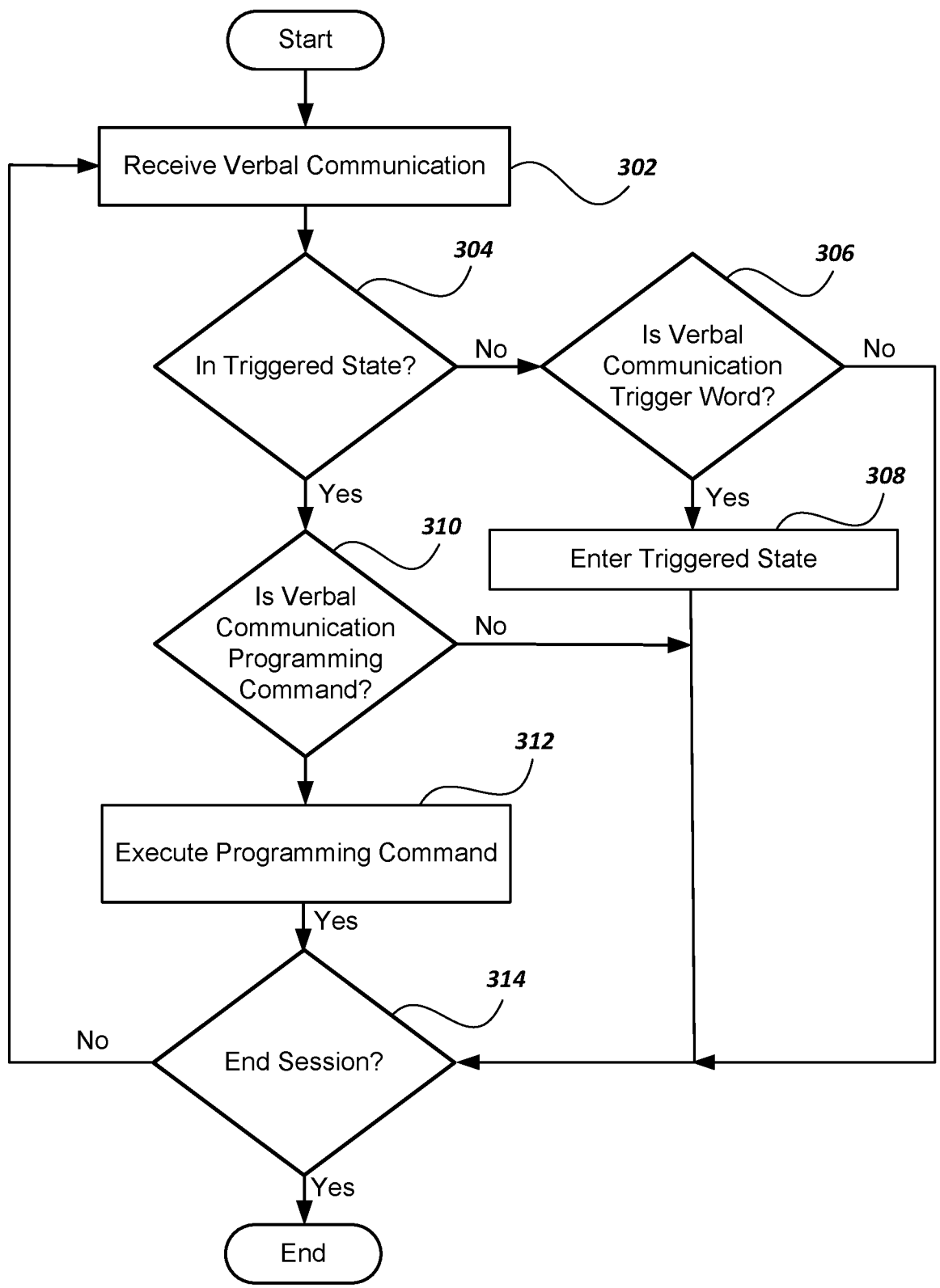
FIG. 3 is a flowchart of one embodiment of operation of a voice command handler for a programming device of a stimulation system.

FIG. 3 is a flowchart of one embodiment of operation of a voice command handler. In step 302, the voice command handler receives a verbal communication. For example, the microphone 213 (FIG. 2) of, or attached to, a CP picks up a word or words from the surrounding.

In step 304, the voice command handler queries if the voice command handler or CP is in the triggered state. If not, in step 306, the voice command handler determines whether the verbal communication is a trigger word. For example, the voice command handler can compare the verbal communication (which may be rendered into text or other suitable form) to a trigger word or a list of trigger words. In at least some embodiments, the CP has a default trigger word(s). In at least some embodiments, the CP allows a user to change the default trigger word(s) to a user-selected trigger word(s) (which may be restricted so that the user cannot select a programming command).

If the verbal communication is not a trigger word, then the voice command handler proceeds to step 314 described below. If the verbal communication is a trigger word, then in step 308 the voice command handler or CP enters the triggered state.

Returning to step 304, if the voice command handler is in the triggered state then in step 310 the voice command handler queries if the verbal communication is a programming command. In at least some embodiments, the CP has a default set of programming commands. In at least some embodiments, the CP allows a user to change one or more of the programming commands or to add to or otherwise modify the set of programming commands.

If the verbal communication is not a programming command, then the voice command handler proceeds to step 314 described below. If the verbal command is a programming command, then in step 312 the voice command handler or CP executes the programming command.

This procedure continues until it is determined that the session ends in step 314.

Figure 4:
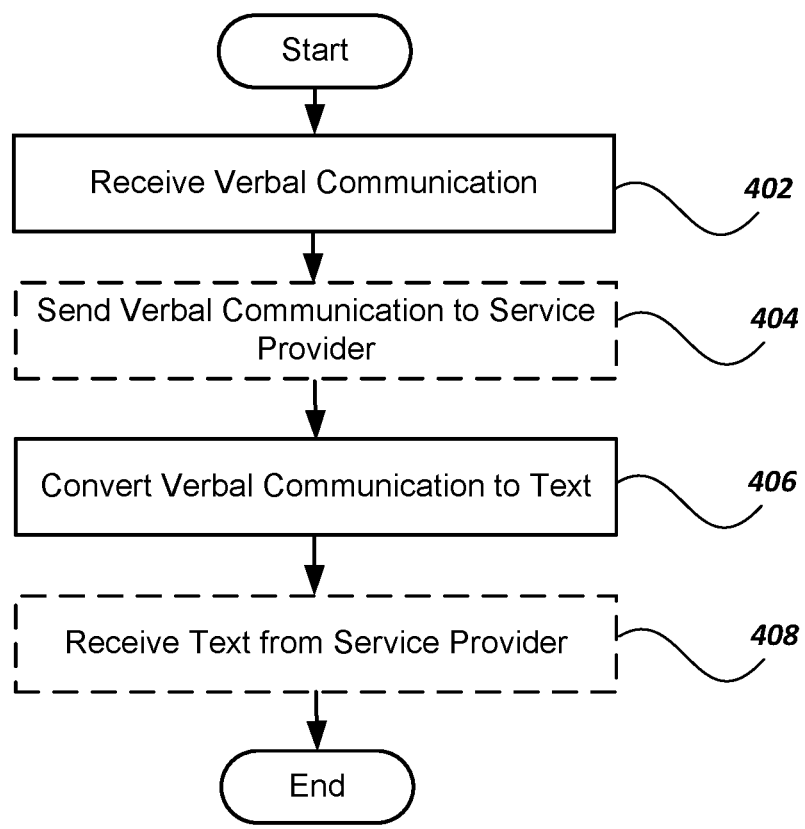
FIG. 4 is a flowchart of one embodiment of a method for determining the content of a verbal communication by the voice command handler.

FIG. 4 is flowchart of one embodiment of a method for determining the content of a verbal communication by the voice command handler. This method can represent or replace step 302 in FIG. 3. In step 402, the voice command handler receives a verbal communication. In step 406, the verbal communication is converted to text (or any other suitable format). The term "text" as used herein refers to a machine-readable representation of the verbal communication which may or may not be readable by a user.

In at least some embodiments, the voice command handler may have speech-to-text software which can perform the conversion and steps 402 and 406 are only performed in this method. In other embodiments, the method includes optional steps 404 and 408. In optional step 404, the voice command handler may send the verbal communication to a local or non-local service provider to produce the speech-to-text conversion using a speech-to-text application in step 406. In step 408, the voice command handler receives the text from the service provider.

Figure 5:
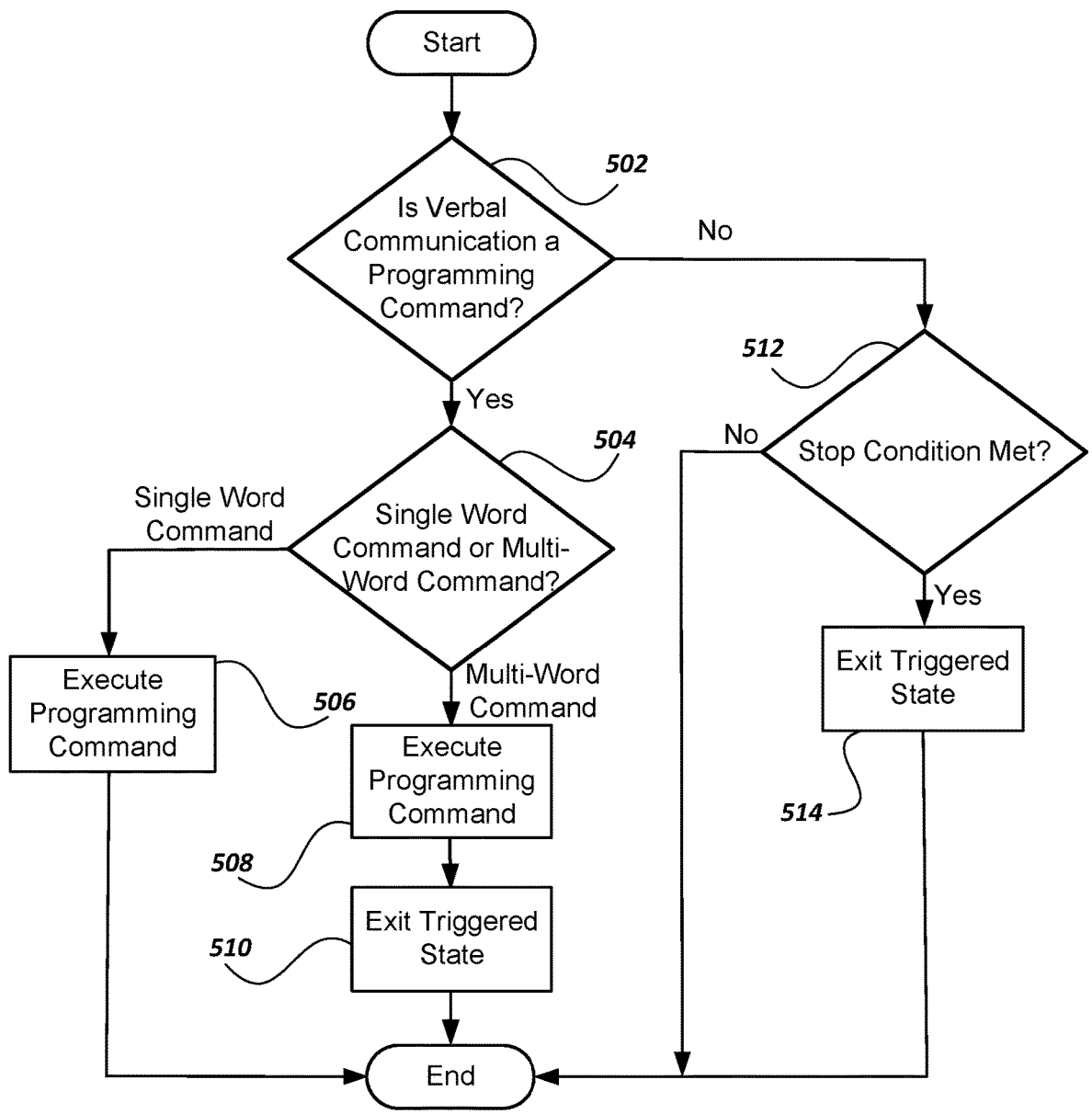
FIG. 5 is a flowchart of one embodiment of a method for determining the disposition of a verbal communication when the voice command handler or CP is in the triggered state.

FIG. 5 is a flowchart of one embodiment of a method for determining the disposition of a verbal communication when the voice command handler or CP is in the triggered state. The method embodiment in FIG. 5 can represent or replace steps 310 and 312 of FIG. 2.

In step 502 the voice command handler queries if the verbal communication is a programming command. If the verbal communication is a programming command, in step 504 the voice command handler queries whether the programming command is a single word command or a multi-word command. Examples of single word command and multi-word commands are provided below. In at least some embodiments, the CP has a default set of single word commands. In at least some embodiments, the CP allows a user to change one or more of the single word commands or to add to or otherwise modify the set of single word commands. In at least some embodiments, the CP has a default set of multi-word commands. In at least some embodiments, the CP allows a user to change one or more of the multi-word commands or to add to or otherwise modify the set of multi-word commands.

If the programming command is a single word command, then in step 506, the voice command handler or CP executes the programming command. In at least some embodiments as exemplified in FIG. 5, the voice command handler remains in the triggered state to allow multiple single word commands to be issued with requiring that the trigger word be presented prior to each single word command.

In other embodiments, the voice command handler exits the triggered state after step 506 and the trigger word is required prior to the next programming command. In these embodiments, receiving a single word command can be an end condition for the triggered state.

Returning to step 504, if the programming command is a multi-word command, then in step 508, the voice command handler or CP executes the programming command. In step 510, the voice command handler exits the triggered state. In at least some embodiments, receiving a multi-word command is an end condition for the triggered state. In other embodiments, step 510 is skipped, and the voice command handler remains in the triggered state.

In at least some embodiments, the voice command handler only recognizes a multi-word command if the trigger word is provided immediately preceding the multi-word command. In some embodiments, the voice command handler may query whether the trigger word was the immediately preceding verbal communication to the multi-word command prior to preceding to steps 508 and 510 and, if this condition is not met, then the voice command handler will instead execute steps 512 and 514, as described below.

Returning to step 502, if the verbal communication is not a programming command, then in step 512 the voice command handler determines if a stop condition is met. For example, the voice command handler may determine that the clinician has stopped issuing commands because this verbal communication is not a programming command. As another example, the voice command handler may determine that the clinician has stopped issuing commands because a number of sequential verbal communications are not programming commands. The number can be set at, for example, two, three, four, five, or more sequential verbal communications that are not programming commands and, in some embodiments, this number may be set or modified by the user. Examples of other stop conditions include, but are not limited to, a pause of a period of time (for example, 10, 15, 30, or 45 seconds or 1, 2, 5, 10, or 15 minutes) without a verbal communication, or the like or any combination thereof. If the stop condition is met, in step 514, the voice command handler or CP exits the triggered state. If the stop condition is not met, then the voice command handler or CP automatically ends the process.

The flowchart of FIG. 5 is repeated for each verbal communication.

In at least some embodiments, the voice command handler only accepts multi-word commands that are immediately proceeded by the trigger word. In at least some of these embodiments, the clinician can voice multiple single word commands without repeating the trigger word each time, but each multi-word command requires a trigger word. In other embodiments, each programming command, whether it is single word command or multi-word command, must be proceeded by the trigger word.

In at least some embodiments, once in the triggered state, the voice command handler may determine continuously or periodically if a stop condition has been reached, such as if there is a pause of a period of time (for example, 10, 15, 30, or 45 seconds or 1, 2, 5, 10, or 15 minutes) without a verbal communication.

Figure 6:
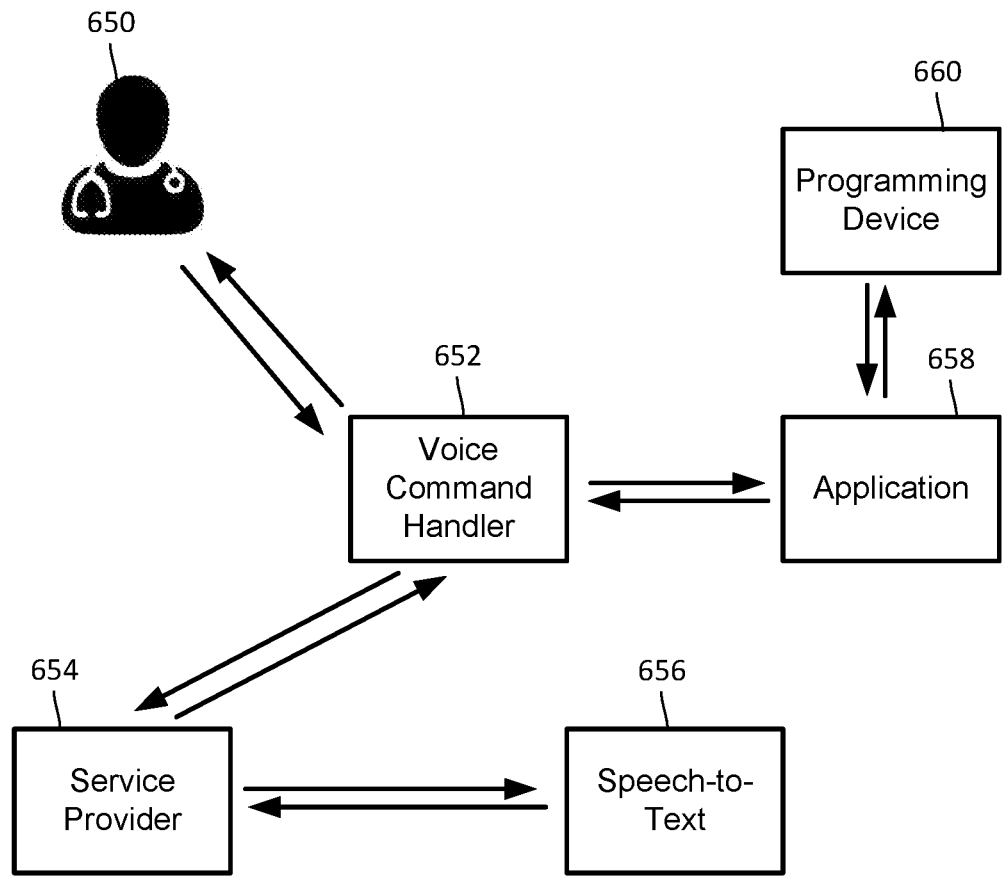
FIG. 6 is a schematic illustration of a workflow for a voice command handler of a programming device of a stimulation system.

FIG. 6 illustrates one embodiment of a workflow for a voice command handler. The clinician 650 (or other programmer or user) speaks a verbal command and the voice command handler 652, which is in listening mode, records the verbal command. The voice command handler 652 delivers the recorded verbal command to a service provider 654 (such as Google Services). For example, the voice command handler 652 may package the verbal command as a byte buffer or any other suitable type of package or file (for example, a sound file).

The service provider 654 converts the verbal command into text using a speech-to-text application 656 (such as Google Speech or any other suitable speech interpretation software). For example, the text may be a JSON object or any other suitable object, package, or file format. The service provider 654 sends the text command back to the voice command handler 652. In other embodiments, the voice command handler 652 may have a speech-to-text application 656 and not require a service provider 654.

The voice command handler 652 parses and categorizes the received text to determine if it is (or contains) a trigger word or a programming command (e.g., a single word command or a multi-word command.) If the received text is a trigger word, the voice command handler 652 is triggered to expect one or more programming commands. If the received text is not a trigger word or not a programming command, the voice command handler 652 does nothing if it has not been triggered or, if the voice command handler has been triggered, checks whether a stop condition has been met, as described herein, to enter an untriggered state. If the received text is a programming command and the voice command handler 652 has been triggered, then the voice command handler matches the received text to a programming command.

In at least some embodiments, the voice command handler 652 activates an application 658 (or other program or subroutine or the like) on the programming device 660 that enacts the programming command on the programming device 660. For example, the application 658 may be a managed DLL or other arrangement that allows the application 658 to enact programming commands or UI selections or the like based on the programming commands. In at least some embodiments, the application 658 may perform the equivalent of selecting a UI control based on the programming command. In at least some embodiments, the programming commands issued by the clinician through the voice command handler 652 are subject to the same restrictions or requirements as the selection of the corresponding UI controls. For example, there may a restriction on the maximum stimulation amplitude that is applied whether the clinician uses the UI controls to increase amplitude or uses the voice command handler 652 to increase amplitude (using, for example, a verbal command such as "Increase"). In at least some embodiments, the voice command handler 652 may include all the features and operations of the application 658 so that a separate application is not needed.

In at least some embodiments, the programming device 660 returns a response to the application 658 if the programming command has been successfully enacted or if an error has occurred. In at least some embodiments, the application 658 returns a response to the voice command handler 652 if the programming command has been successfully enacted or if an error has occurred. In at least some embodiments, one or more of the voice command handler 652, application 658, or programming device 660 produces an audible or visual indication that the programming command has been enacted so that the clinician 650 can verify whether the command was successful or not. For example, an audible click or chime may be produced if the command is successful. In at least some embodiments, a different audible or visual indication is produced if the programming command was not implemented or not successful or if an error occurred. This procedure continues as the clinician continues to issue commands.

Examples of single word commands include, but are not limited to, the following (with the result of the command in parenthesis): Increase (increase amplitude), Decrease (decrease amplitude), Small (implement small step size for amplitude, etc.), Large (implement large step size for amplitude, etc.), Cancel (cancel previous command), Continue or Okay (continue previous commands), Stimulation or Stim (stimulation on), Off or Stop (stimulation off), Widen (increase pulse width), Narrow (decrease pulse width), Left or Counterclockwise (rotate stimulation left), Right or Clockwise (rotate stimulation right), Up or Superior (move stimulation upward or distally along lead), Down or Inferior (move stimulation downward or proximally along lead), Steering (set steering mode), Custom (set custom mode), Focus (angularly focus stimulation), or Spread (angularly spread stimulation).

At least some of these commands are particularly relevant to directional stimulation leads (for example, leads with segmented electrodes) such as, for example, Focus, Spread, Left or Counterclockwise, or Right or Clockwise. Examples of directional leads and leads with segmented electrodes can be found in U.S. Patent Application Publications Nos. 2010/0268298; 2011/0005069; 2011/0078900; 2011/0135803; 2011/0135816; 2011/0135817; 2011/0135818; 2011/0078900; 2011/0238129; 2011/0363500; 2012/0016378; 2012/0046710; 2012/0071949; 2012/0165911; 2012/0197375; 2012/0203366; 2012/0203320; 2012/0203321; 2013/0197602; 2013/0261684; 2013/0325091; 2013/0367587; 2014/0039587; 2014/0353501; 2014/0358209; 2014/0358210; 2015/0018915; 2015/0021817; 2015/0045864; 2015/0021817; 2015/0066120; 2013/0197424; 2015/0151113; 2014/0358207; and U.S. Pat. Nos. 8,483,237; 10,441,800; 10,603,498; 10,716,942; and 10,780,282, all of which are incorporated herein by reference in their entireties.

Other single word commands can be used to mark therapeutic effects or side effects in a patient's record or on a clinical effects chart. Examples of single word commands include, but are not limited to, the following: Rigidity, Tremor, BradyKinesia, Gait, Turning, Posture, Freezing, Balance, Dystonia, Speech, Muscle (for muscle pulling), Ocular (for an ocular effect), Mania, Nausea, Parasthesia, Discomfort, Dyskinesia, Dizziness, or Depression.

One example of a multi-word command is in the form of a command phrase and user selected number such as, for example, "Set Rigidity to 4" or "Set [x] to [y]" where [x] is any of the therapeutic effects or side effects or a stimulation setting (for example, amplitude, pulse width, pulse frequency, stimulation duration, or the like) listed in the preceding paragraph and [y] is a numerical value corresponding to the user selected number. Other examples can be "Set [x]" or "Remove [x]" to set or remove the specified therapeutic effect or side effect from the patient's record or the clinical effects map. In at least some embodiments, these multi-word commands can be used to fill in a clinical effects map by providing an annotation at the current stimulation amplitude and electrode selection. Non-limiting examples of clinical effects maps can be found in, for example, U.S. Pat. Nos. 9,474,903; 9,561,380; 9,643,014; 9,643,017; 9,959,388; 10,071,249; 10,350,404; 10,603,498; 10,625,082; 10,716,505; 10,716,942; and 10,780,282, all of which are incorporated herein by reference in their entireties.

Examples of other multi-word commands include, but are not limited to, the following (with the result of the command in parenthesis): Set to Small (set small step size), Set to Large (set large step size), Stop Therapy or Stop Therapies or Stop All (stop current therapy(ies)), Stimulation On or Stim On (turn on stimulation), Stimulation Off or Stim Off (turn off stimulation), Program Tab (navigate to the program tab), Configure Tab (navigate to the configure tab), Set Program (program), Set Pulse Width or Pulse Width (set pulse width), or Set Rate or Set Pulse Rate (set pulse rate). In at least some instances, the multi-word command may be followed by a number to which the particular parameter is to be set.

Returning to FIG. 2, in at least some embodiments, in addition to or as an alternative to, the trigger word, a CP/RC 206 (or other programming device) can have a VCH actuator 221, such as a foot pedal, button device, clinician remote control, or other suitable device, that can be actuated by the clinician or other person. Actuation of the VCH actuator 221 is equivalent to speaking the trigger word and indicates to the voice command handler that the clinician will speak one or more commands. In at least some embodiments, the voice command handler requires or can be selected to require actuation of the VCH actuator 221 instead of the use of trigger word. In other embodiments, the clinician has the choice whether to use the trigger word or the VCH actuator 221. The VCH actuator 221 can be coupled to the CP/RC 206 (or other programming device) using any suitable wired or wireless arrangement. In at least some embodiments, upon actuation, the VCH actuator 221 provides a signal to the CP/RC 206 of the actuation.

In at least some embodiments, the VCH actuator feature can be bound to a keyboard key (which may be user selectable or modifiable). In at least some embodiments, the user can select the keyboard key to enact stimulation programming commands without needing the trigger word.

Figure 7:
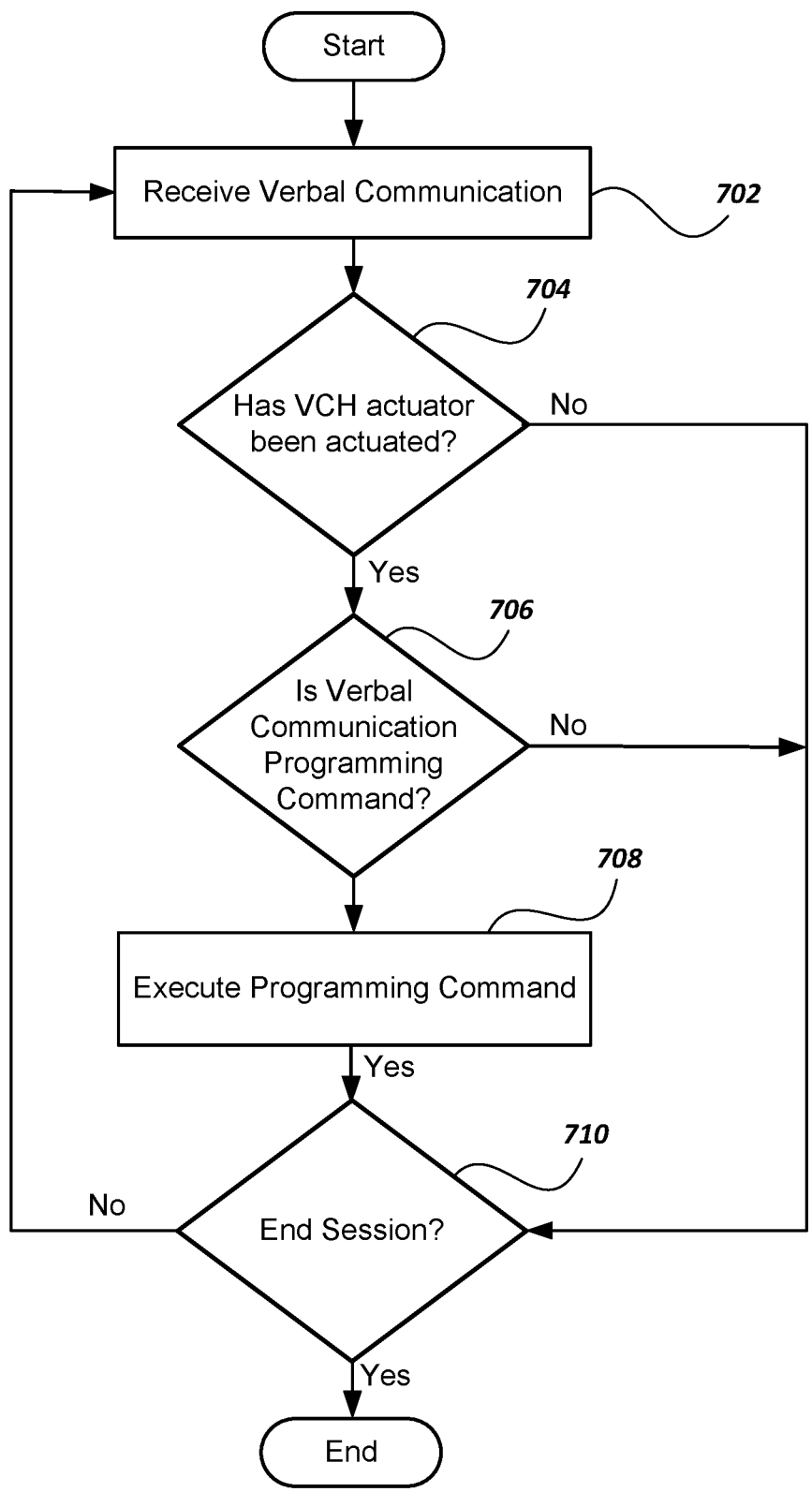
FIG. 7 is a flowchart of one embodiment of operation of a voice command handler for a programming device of a stimulation system using a VCH actuator.

FIG. 7 is a flowchart of one embodiment of operation of a voice command handler. In step 702, the voice command handler receives a verbal communication. For example, the microphone of, or attached to, a CP picks up a word or words from the surrounding.

In step 704, the voice command handler queries if the VCH actuator was actuated prior to the verbal communication. In at least some embodiments, there may be a requirement that the time between the actuation of the VCH actuator and receiving the verbal communication be no more than predefined time period (for example, 5, 10, or 15 seconds.) In yet other embodiments, the voice command handler may query if the VCH actuator was actuated after the verbal communication within a predefined time period (for example, 5, 10, or 15 seconds.) If the VCH actuator has not been actuated, then the voice command handler proceeds to step 710 described below.

In other embodiments, step 704 is skipped, and the voice command handler is only in the listening mode after actuation of the VCH actuator. The listing mode may only be active for a predefined time period (for example, 5, 10, or 15 seconds) after actuation of the VCH actuator. In these embodiments, step 702 is only performed when the voice command handler is in the listening mode.

If the VCH actuator has been actuated, then in step 706 the voice command handler queries if the verbal communication is a programming command. In at least some embodiments, the CP has a default set of programming commands. In at least some embodiments, the CP allows a user to change one or more of the programming commands or to add to or otherwise modify the set of programming commands.

If the verbal communication is not a programming command, then the voice command handler proceeds to step 710 described below. If the verbal command is a programming command, then in step 708 the voice command handler or CP executes the programming command.

This procedure continues until it is determined that the session ends in step 710.

In at least some embodiments, the VCH actuator 221 must be actuated prior to (or, in some embodiments, after) each programming command. In other embodiments, actuation of the VCH actuator 221 may place the voice command handler or CP in the triggered state and allow the clinician to provide multiple single word commands (or, in some embodiments, multiple programming commands of any type) without another actuation of the VCH actuator 221 unless a stop condition (as described above) is met.

It will be understood that each block of the flowchart illustration, and combinations of blocks in the flowchart illustration and methods disclosed herein, can be implemented by computer program instructions. These program instructions may be provided to a processor to produce a machine or engine, such that the instructions, which execute on the processor, create means for implementing the actions specified in the flowchart block or blocks or engine disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computing device. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device. The computer program instructions can be stored locally or nonlocally (for example, in the Cloud).

The above specification and examples provide a description of the arrangement and use of the invention. Since many embodiments of the invention can be made without departing from the spirit and scope of the invention, the invention also resides in the claims hereinafter appended.

What is claimed as new and desired to be protected is:

1. A method for programming a stimulation device of a stimulation system using a programming device, the method comprising:

providing a predefined set of programming commands for the programming device, wherein the predefined set of programming commands comprises a first programming command increasing a stimulation amplitude and a second programming command comprises decreasing the stimulation amplitude;

receiving a verbal communication by a voice command handler of the programming device or in communication with the programming device;

determining whether the verbal communication is a trigger word and, when the verbal communication is the trigger word, entering a triggered state, wherein, after entering the triggered state, the programming device remains in the triggered state until a one of at least one stop condition is met; and when in the triggered state, determining whether the verbal communication is one of the programming commands and, when the verbal communication is one of the programming commands, executing the one of the programming commands and then remaining in the triggered state for receiving another programming command, wherein the at least one stop condition comprises at least one of: (1) not receiving verbal communication for a predefined time period of at least 10 seconds, or (2) receiving a predefined number of consecutive verbal communications that are not any of the programming commands.

2. The method of claim 1, wherein the predefined time period is at least 15 seconds.

3. The method of claim 1, wherein the predefined number is at least three.

4. The method of claim 1, wherein determining whether the verbal communication is one of the programming commands comprises comparing the verbal communication to the predefined set of programming commands.

5. The method of claim 4, wherein the predefined set of programming commands comprises a plurality of single word commands.

6. The method of claim 4, wherein the predefined set of programming commands comprises a plurality of multi-word commands.

7. The method of claim 6, wherein at least one of the multi-word commands has a form of a command phrase and a user-selected number.

8. The method of claim 1, further comprising converting the verbal communication to a machine-readable text.

9. The method of claim 1, further comprising delivering the verbal communication to a service provider for the purpose of converting the verbal communication to a machine-readable test and receiving, from the service provider, the machine-readable text.

10. The method of claim 1, further comprising providing an audible or visual indication after executing the one of the programming commands.

11. A method for programming a stimulation device of a stimulation system using a programming device, the method comprising:
providing a predefined set of programming commands for the programming device, wherein the predefined set of programming commands comprises a plurality of single word commands and a plurality of multi-word commands, wherein the single word commands comprise a first programming command increasing a stimulation amplitude and a second programming command comprises decreasing the stimulation amplitude;
receiving a verbal communication by a voice command handler of the programming device or in communication with the programming device;
determining whether the verbal communication is a trigger word and, when the verbal communication is the trigger word, entering a triggered state, wherein, after entering the triggered state, the programming device remains in the triggered state until a one of at least one stop condition is met;
when in the triggered state, determining whether the verbal communication is one of the single word commands and, when the verbal communication is one of the single word commands, executing the one of the single word commands and remaining in the triggered state; and
when in the triggered state, determining whether the verbal communication is one of the multi-word commands and, when the verbal communication is one of the multi-word commands, executing the one of the multi-word commands and entering a non-triggered state.

12. The method of claim 11, wherein the at least one stop condition comprises not receiving verbal communication for a predefined time period of at least 15 seconds.

13. The method of claim 11, wherein the at least one stop condition comprises receiving a predefined number of consecutive verbal communications that are not the trigger word, any of the single word commands, or any of the multi-word commands, wherein the predefined number is at least three.

14. The method of claim 11, wherein at least one of the multi-word commands has a form of a command phrase and a user-selected number.

15. The method of claim 11, further comprising converting the verbal communication to a machine-readable text.

16. The method of claim 11, further comprising delivering the verbal communication to a service provider for the purpose of converting the verbal communication to a machine-readable test and receiving, from the service provider, the machine-readable text.

17. The method of claim 11, further comprising providing an audible or visual indication after executing the one of the single word commands or the one of the multi-word commands.

* * * * *